United States Patent
Hauger et al.

(10) Patent No.: US 11,836,920 B2
(45) Date of Patent: Dec. 5, 2023

(54) APPARATUS AND METHOD FOR CLASSIFYING A BRAIN TISSUE AREA, COMPUTER PROGRAM, NON-VOLATILE COMPUTER READABLE STORAGE MEDIUM AND DATA PROCESSING APPARATUS

(71) Applicant: Carl Zeiss Meditec AG, Jena (DE)

(72) Inventors: Christoph Hauger, Aalen (DE); Stefan Saur, Aalen (DE); Gerald Panitz, Bopfingen (DE)

(73) Assignee: Carl Zeiss Meditec AG, Jena (DE)

( * ) Notice: Subject to any disclaimer, the term of this patent is extended or adjusted under 35 U.S.C. 154(b) by 432 days.

(21) Appl. No.: 17/206,059

(22) Filed: Mar. 18, 2021

(65) Prior Publication Data
US 2021/0295519 A1    Sep. 23, 2021

(30) Foreign Application Priority Data
Mar. 18, 2020    (DE) ..................... 10 2020 107 519.7

(51) Int. Cl.
*G06K 9/00*    (2022.01)
*G06T 7/00*    (2017.01)
(Continued)

(52) U.S. Cl.
CPC .......... *G06T 7/0014* (2013.01); *A61N 1/3606* (2013.01); *G06T 7/38* (2017.01);
(Continued)

(58) Field of Classification Search
CPC . G06T 2207/30096; G06T 2207/30104; G06T 2207/30016; G06T 2207/30101;
(Continued)

(56) References Cited

U.S. PATENT DOCUMENTS

| | | | | |
|---|---|---|---|---|
| 5,465,718 A | * | 11/1995 | Hochman | .......... A61B 5/14553 |
| | | | | 600/431 |
| 6,233,480 B1 | * | 5/2001 | Hochman | ............ A61B 5/4094 |
| | | | | 600/476 |

(Continued)

FOREIGN PATENT DOCUMENTS

| | | |
|---|---|---|
| DE | 102008051950 A1 | 7/2010 |
| EP | 1838206 B1 | 4/2018 |

OTHER PUBLICATIONS

U.S. Appl. No. 17/106,102, filed Nov. 28, 2020, Patrick Hoyer.

(Continued)

*Primary Examiner* — Atiba O Fitzpatrick
(74) *Attorney, Agent, or Firm* — Ewers IP Law PLLC; Falk Ewers (57) ABSTRACT

An apparatus for classifying a brain tissue area as functional or non-functional by a stimulation of the brain includes a receiver unit for receiving information about a performed stimulation, a recording device for recording images that represent the brain tissue area, a detection unit for detecting a change in perfusion in the brain tissue area, and a classification unit configured to determine with the information whether there is a correlation between the performed stimulation and the detected change in perfusion, and to classify the brain tissue area as functional or as non-functional. The recording device is an endomicroscope for recording endomicroscopic images of the brain tissue area with a spatial resolution better than 20 μm and a frame rate of at least 0.4 frames per second. The detection unit is configured to detect a change in perfusion based on the positions of certain tissue structures in the recorded images.

11 Claims, 4 Drawing Sheets

(51) Int. Cl.
 *G06T 7/38* (2017.01)
 *G16H 30/40* (2018.01)
 *A61N 1/36* (2006.01)
(52) U.S. Cl.
 CPC ......... *G16H 30/40* (2018.01); *G06T 2207/10* (2013.01); *G06T 2207/20081* (2013.01); *G06T 2207/30016* (2013.01); *G06T 2207/30104* (2013.01)
(58) Field of Classification Search
 CPC ....... G06T 7/0014; G06T 7/246; G06T 7/248; G06T 7/20; G02B 23/24; G02B 23/243; G02B 23/2415; A61N 1/0456; A61B 5/0042; A61B 5/4064; A61B 2034/2065
 See application file for complete search history.

(56) References Cited

U.S. PATENT DOCUMENTS

| | | | |
|---|---|---|---|
| 6,671,540 B1* | 12/2003 | Hochman | A61B 5/14553 600/431 |
| 7,598,492 B1 | 10/2009 | Krzeczowski et al. | |
| 8,057,083 B2 | 11/2011 | Harris | |
| 9,095,255 B2 | 8/2015 | Fanenbruck | |
| 9,801,549 B2 | 10/2017 | Panitz et al. | |
| 9,921,406 B2 | 3/2018 | Wang et al. | |
| 2002/0099295 A1* | 7/2002 | Gil | A61B 5/4064 600/323 |
| 2003/0236458 A1* | 12/2003 | Hochman | A61B 5/0059 600/431 |
| 2006/0245640 A1 | 11/2006 | Szczuka | |
| 2009/0054788 A1 | 2/2009 | Hauger et al. | |
| 2009/0092363 A1 | 4/2009 | Daum et al. | |
| 2010/0130869 A1 | 5/2010 | Hauger et al. | |
| 2010/0157037 A1 | 6/2010 | Iketani et al. | |
| 2010/0157308 A1 | 6/2010 | Xie | |
| 2011/0043649 A1 | 2/2011 | Nakada | |
| 2014/0232848 A1 | 8/2014 | Schwedt et al. | |
| 2015/0289765 A1* | 10/2015 | Panitz | A61B 5/742 600/476 |
| 2016/0035093 A1* | 2/2016 | Kateb | G02B 21/0012 382/131 |
| 2016/0051131 A1 | 2/2016 | Jeong et al. | |
| 2017/0340212 A1* | 11/2017 | Lin | G16H 30/40 |
| 2017/0340260 A1* | 11/2017 | Chowdhury | A61B 5/14551 |
| 2018/0005361 A1 | 1/2018 | Bulyshev | |
| 2018/0020922 A1 | 1/2018 | Liu et al. | |
| 2018/0256025 A1 | 9/2018 | Yi et al. | |
| 2020/0265211 A1 | 8/2020 | Nasrabadi et al. | |
| 2020/0268911 A1* | 8/2020 | Albert | G01R 33/4806 |

OTHER PUBLICATIONS

A. Raabe, et al., Laser Doppler imaging for intraoperative human brain mapping, Nov. 2008.
M. Goetz, et al., Dynamic in vivo Imaging of Microvasculature and Perfusion by Miniaturized Confocal Laser Microscopy, Jul. 30, 2008.
Vivek J. Srinivasan, et al., Quantitative cerebral blood flow with Coherence Tomography, 2010.
Jiang You, et al., Optical coherence Doppler tomography for quantitative cerebral blood flow imaging, 2014.
Martin Oelschlgel, et al., Interoperative Optical imaging of metabolic changes after direct cortical stimulation—a clinical tool for guidance during tumor resection?, Feb. 5, 2018.
Office Action issued in German Patent Application No. DE 10 2020 107 519.7 (from which this application claims priority), dated Jan. 27, 2021 and English language machine translation thereof.
A.S. Fruchter and R.N. Hook, Drizzle "A Method for the Linear Reconstruction of Undersampled Images" , Publications of the Astronomical Society of the Pacific, 114:144152, 2002 Feb. 2002.
Farsiu, Sina; et al.: Advances and challenges in super-resolution. International Journal of Imaging Systems and Technology, 2004, Nr. 2, Seiten 47-57.
B. Wronski et al. "Handheld Multi-Frame Super-Resolution" ACM Trans. Graph., vol. 38, No. 4, Article 28, Jul. 2019.

* cited by examiner

APPARATUS AND METHOD FOR CLASSIFYING A BRAIN TISSUE AREA, COMPUTER PROGRAM, NON-VOLATILE COMPUTER READABLE STORAGE MEDIUM AND DATA PROCESSING APPARATUS

CROSS REFERENCE TO RELATED APPLICATIONS

This application claims priority to German patent application DE 10 2020 107 519.7, filed Mar. 18, 2020, the entire content of which is incorporated herein by reference.

TECHNICAL FIELD

The present disclosure relates to an apparatus and a method for classifying a brain tissue area as functional or non-functional with the aid of a stimulation of the brain. Additionally, the disclosure relates to a computer program for classifying a brain tissue area as functional with the aid of a stimulation of the brain, a non-volatile computer readable storage medium with such a computer program, and a data processing apparatus.

BACKGROUND

In the course of neurosurgical interventions for the resection of tumor tissue, the aim of the surgeon is complete removal of the malignant tissue while at the same time preserving and specifically sparing healthy, functional tissue. After opening the skull and exposing the surface of the brain, in many cases these different types of tissue are not distinguishable from one another on a purely visual basis in the exposed portion of brain tissue, which makes it more difficult to achieve the stated aims of the intervention.

One option for identifying functional tissue consists of stimulating certain functions which lead to electrical responses of brain tissue areas and capturing the electrical responses with electrodes. Since the electrical responses are captured with electrodes that contact the brain tissue, it is not possible to completely preclude mechanical damage to the brain tissue or a contamination of the brain tissue.

A further option is offered by linking the stimulation with optical imaging, in which it is not the electrical responses of the brain tissue areas that are captured but changes in perfusion, which occur in the brain tissue areas activated by the stimulation as a consequence of the stimulation. These changes in perfusion lead to changes in the optical properties of the activated brain tissue areas, which can be recorded by a camera and subsequently be evaluated. On the basis of the changes in the optical properties of the brain tissue captured in this way, the functional state and/or the type of tissue in the region of the stimulation is deduced. Methods in which images are recorded before and/or during a stimulation and the functional brain areas are determined by evaluating the images recorded are described for example in Oelschlagel et al. "Intraoperative optical imaging of metabolic changes after a direct cortical stimulation—a clinical tool for guidance during tumor resection?" in Biomed. Eng. Biomed. Tech. 2018, appearing online on Feb. 5, 2018, available at https://doi.org/10.1515/bmt-2017-0156, in U.S. Pat. No. 9,095,255 B2 and in U.S. Pat. No. 9,801,549 B2. This procedure is time-consuming on account of the low intensity of the optical signals.

US 2010/0130869 A1 or A. Raabe et al. "Laser Doppler Imaging for Intraoperative Human Brain Mapping", Neuroimage 2009, February 15, 44 (4), pages 1284 to 1489, DOI: 10.1016 has described the detection of changes in perfusion with laser Doppler imaging (LDI). Here, as a characteristic for the perfusion, the flow speed of the blood in blood vessels of the brain tissue areas is detected on the basis of the Doppler effect. Since a stimulation leads to a change in perfusion and hence to a change in the flow speed of the blood, functional brain tissue areas can be detected with laser Doppler imaging. However, the integration of laser Doppler imaging in a surgical microscope or in an endoscope is complex, just like the quantitative evaluation of the measurements. The same applies if a change in perfusion is detected with optical coherence tomography (OCT), as is described, for example, in US 2018/0020922 A1, US 2018/0256025 A1, V. J. Srinivasan: "Quantitative cerebral blood flow with optical coherence tomography", Opt. Express, Vol. 18, No. 3, Jan. 22, 2010, pages 2477-2494, and J. You: "Optical coherence Doppler tomography for quantitative cerebral blood flow Imaging" in Biomedical Optics Express Vol. 5, No. 9, published Aug. 28, 2014, pages 3217-3230. As a rule, this type of detection is also based on the Doppler effect, and so the integration of an OCT in a surgical microscope or an endoscope for the purposes of measuring perfusion is also complex, like the integration of laser Doppler imaging, and requires a complex evaluation.

SUMMARY

It is therefore an object of the present disclosure to provide an apparatus and a method for classifying a brain tissue area as functional or non-functional, which can be integrated in an endomicroscope or carried out by an endomicroscope more easily than the apparatuses and methods set forth at the outset. Further objects of the present disclosure include providing a computer-implemented method, a computer program of a non-volatile computer readable storage medium, and a data processing apparatus, which facilitate a perfusion measurement that need not resort to the Doppler effect.

The first object is achieved by an apparatus and a method, and a computer-implemented method for classifying a brain tissue area as functional or non-functional with the aid of a stimulation of the brain as described herein.

An apparatus according to an aspect of the disclosure for classifying a brain tissue area as functional or non-functional with the aid of a stimulation of the brain includes a receiver unit for receiving information items about a performed stimulation. The information about the performed stimulation can contain, for example, the start time and/or the end time of the stimulation and, in particular, can contain both the start time and the end time. However, there alternatively also is the option of the information containing the start time and the end time of a stimulation. As a further alternative, the information about a performed stimulation can also be integrated in at least one of the recorded images, for example by virtue of the image recorded at the start of the stimulation being marked accordingly. In particular, in this case, different markings for the start and the end of a stimulation can also be integrated into the images recorded at the respective point in time. If the information is present in the recorded images in the form of a marking or a plurality of markings, the receiver unit can contain an extraction module for extracting the information from the recorded images. The apparatus further includes a recording device for recording images that represent the brain tissue area. By way of example, the images can be fluorescence images, i.e., images that have been recorded on the basis of fluorescence light emitted by the brain tissue area. Alternatively, there is also the option of the recorded images having been recorded on the basis of reflected light, wherein, in particular, use can also be made of a hyperspectral sensor, i.e., a sensor that is able to record images in more than three wavelengths. Apart from fluorescence or reflected light, the image generation can also be based on Raman scattering or multiphoton fluorescence. Moreover, there is the option of combining images from different depths to form a so-called z-stack, for example within the scope of optical coherence tomography (OCT). The apparatus further includes a detection unit for detecting a change in perfusion in the brain tissue area on the basis of recorded images. Typically, the start of a stimulation leads to an increase in perfusion in the stimulated tissue and the end of a stimulation leads to a reduction in perfusion. The apparatus also includes a classification unit which is configured to determine with the aid of the information about a performed stimulation whether there is a correlation between the performed stimulation and the detected change in perfusion, and which is moreover configured to classify the brain tissue area as functional if it determines a correlation and classify the brain tissue area as non-functional if it does not determine a correlation. In particular, the correlation can be a time correlation. By way of example, if the information about a performed stimulation contains the start time and/or the end time of a stimulation and the images are provided with a timestamp, the classification unit can use the time information items to check whether there is a time correlation between the start and/or the end of a stimulation and the occurrence of a change in perfusion. By contrast, if the information about the stimulation is available, as described above, in the form of markings in the images, the correlation can lie in the fact that, for instance, a change in perfusion is determined, for example, in the next or next but one image following the marked image.

According to an aspect of the disclosure, the recording device is an endomicroscope for recording endomicroscopic images of the brain tissue area with a spatial resolution of better than 20 µm, for example 10 µm, 5 µm, 3 µm, 1 µm, 0.7 µm, or better, and a frame rate of at least 0.4 frames per second, typically a frame rate of one frame per second or more. Moreover, the detection unit is configured to detect a change in perfusion on the basis of the position of certain tissue structures in the recorded images.

The disclosure exploits the fact that a change in perfusion leads to a change in the position of certain tissue structures in the stimulated brain tissue area. This change in position can be detected in high-resolution endomicroscopic images and can be used as an indicator for a change in perfusion. Consequently, a change in perfusion can be determined without resorting to the Doppler effect, and so the apparatus can be integrated relatively easily into an endomicroscope. Here, the positions of two tissue structures in the same image are used for detecting a change in perfusion. The detection unit is configured to determine the distance between these tissue structures on the basis of the positions of said tissue structures and detect a change in perfusion on the basis of a change in the distance. Here, it is possible to exploit the circumstance that a change in perfusion leads, as a rule, to a change in the diameters of capillary blood vessels. If the tissue structures in the images are wall sections of capillary blood vessels to be recognized, the distance between the wall sections from one another represented in the image changes with the vessel diameter, and so a change in perfusion can be deduced from a change in the distance between the wall sections.

Additionally, the positions of the same tissue structure in at least two endomicroscopic images recorded at time intervals can be used to detect a change in perfusion. In this case, the certain tissue structures can be, in particular, erythrocytes, i.e., red blood cells, the flow speed of which can be determined on the basis of their positions in successive images and the frame rate at which the images were recorded. In this case, a change in the flow speed signals a change in perfusion. However, it is not mandatory for the detection unit to actually determine the flow speed. It is sufficient for the distance between the position of a red blood cell and its position in the preceding image to be determined for a number of images at a constant frame rate and for the change in this distance to be determined. Here, a lengthening of the distance signals an increase in the flow speed and hence an increase in perfusion while a reduction in the distance signals a reduction in the flow speed and hence a drop in perfusion. Using the combination of a change in the distance between wall sections of capillary blood vessels and a change in the distance between red blood cells in successive images for the purposes of detecting a change in perfusion is advantageous since a change in perfusion is then determined on the basis of two independent processes, increasing the reliability of the detection of a change in perfusion.

In one configuration of the apparatus according to the disclosure, the detection unit includes an input apparatus which allows tissue structures of the brain tissue area represented in the image to be marked in a recorded image. In this way, it is possible to communicate to the detection unit the tissue structures it should use to detect a change in perfusion. In addition or as an alternative thereto, there is the option of the detection unit comprising a recognition module for recognizing at least one type of tissue structures, for instance wall sections of capillary blood vessels, erythrocytes, etc., of the brain tissue area represented in a recorded image. In particular, recognition can be implemented on the basis of morphological criteria in this case. By way of example, a trained neural network can be used to recognize the tissue structures, which trained neural network has been trained with training data records respectively with tissue structure-showing images which contain information about where certain tissue structures can be recognized in the respective image. If the trained neural network should be able to recognize different types of tissue structures, the training data moreover contain information items about what type of structures can be recognized in the images and where the respective type of structure is situated in the images.

As a result of movements of the brain tissue area on account of physiological processes or as a result of trembling when holding the probe of the endomicroscope, the tissue sections represented in the recorded images may be subject to different global rotations and/or translations, i.e., rotations and/or translations that act in the same way on all pixels in the image. In order to be able to compensate these global rotations and/or translations between various images, it is advantageous if the detection unit includes a registration module, with which the recorded images can be registered to one another.

Moreover, the apparatus according to an aspect of the disclosure can include an electrical stimulation apparatus for electrical stimulation of the brain. Here, the electrical stimulation can either be undertaken directly on the brain with electrodes or with an electrical stimulation of the peripheral nervous system by way of electrodes attached to extremities. However, in the case of a conscious patient, the stimulation can also be implemented without a stimulation apparatus, for example by virtue of said patient carrying out certain tasks that lead to the stimulation of certain brain tissue regions.

To facilitate an ergonomically advantageous display of found functional brain tissue areas for a treating physician, the apparatus according to an aspect of the disclosure can include an augmentation apparatus configured to label in an overview image representing a tissue region with a number of brain tissue areas the brain tissue areas classified as functional.

Moreover, a method for classifying a brain tissue area as functional or non-functional during a stimulation of the brain is made available according to the disclosure. The method includes the steps of receiving information items about a performed stimulation, recording images that represent the brain tissue area, checking whether there is a change in perfusion in the brain tissue area on the basis of the recorded images, if the check yields that a change in perfusion is present, determining whether there is a correlation between the performed stimulation and the change in perfusion with the aid of the information items about the performed stimulation, and classifying the brain tissue area as functional if the presence of a correlation is determined and classifying the brain tissue area as non-functional if the presence of a correlation is not determined.

Within the scope of the method according to an aspect of the disclosure, endomicroscopic images of the brain tissue area with a spatial resolution of better than 20 µm, for example 10 µm, 5 µm, 3 µm, 1 µm, 0.7 µm or better, and a frame rate of 0.4 frames per second, in particular a frame rate of one frame per second or more, are recorded as images. The check whether a change in perfusion is present is then implemented on the basis of the position of certain tissue structures in at least one recorded image. Here, the positions of the specific tissue structures are the positions of two different tissue structures in the same image. The distance between these tissue structures is determined on the basis of the positions. A change in perfusion is then detected on the basis of a change in the distance.

The method according to an aspect of the disclosure facilitates the determination of a change in perfusion without resorting to the Doppler effect. This is rendered possible, in particular, by virtue of the endomicroscopic images having a high resolution and a frame rate of at least 0.4 frames per second. The method according to the disclosure can therefore be integrated into an endomicroscope with relative ease.

Within the scope of the method according to an aspect of the disclosure, there is the option of classifying a plurality of brain tissue areas and labeling the classified brain tissue areas in an overview image on the basis of their classification. In this way, it is possible to create overview images in which, e.g., the functional brain tissue areas or the non-functional brain tissue areas are highlighted. However, it is also possible to emphasize both the functional brain tissue areas and the non-functional brain tissue areas, with these then differing from one another in the type of emphasis, for example by virtue of being marked in different colors. In this way, an ergonomically advantageous display of found functional brain tissue areas is facilitated for the treating physician.

Further configurations of the method according to an aspect of the disclosure emerge from the functions which were described with reference to the configurations of the apparatus according to an aspect of the disclosure and which are carried out by the configurations of the apparatus.

Moreover, according to a further aspect of the present disclosure, a computer-implemented method for classifying a brain tissue area as functional or non-functional during a stimulation of the brain is made available. The computer-implemented method includes the steps of receiving information items about a performed stimulation, receiving images that represent the brain tissue area, checking whether there is a change in perfusion in the brain tissue area on the basis of the received images, if the check yields that a change in perfusion is present, determining whether there is a correlation between the performed stimulation and the change in perfusion with the aid of the information items about the performed stimulation, and classifying the brain tissue area as functional if the presence of a correlation is determined and classifying the brain tissue area as non-functional if the presence of a correlation is not determined.

According to an aspect of the disclosure, endomicroscopic images of the brain tissue area with a spatial resolution of better than 20 µm, for example 10 µm, 5 µm, 3 µm, 1 µm, 0.7 µm or better, and a frame rate of at least 0.4 frames per second, in particular a frame rate of at least one frame per second, are received as images within the scope of the computer-implemented method. The check whether a change in perfusion is present is then implemented on the basis of the position of certain tissue structures in at least one recorded image. Here, the positions of the specific tissue structures are the positions of two different tissue structures in the same image. The distance between these tissue structures is determined on the basis of the positions. A change in perfusion is then detected on the basis of a change in the distance.

The computer-implemented method according to an aspect of the disclosure allows the method according to an aspect of the disclosure to be carried out on a computer which is linked to an endomicroscope for receiving the endomicroscopic images and which is possibly linked to a stimulation apparatus for receiving the information items about the stimulation. Advantageous configurations of the computer-implemented method according to the disclosure emerge from the functions which were described with reference to the configurations of the apparatus according to an aspect of the disclosure and which are carried out by the configurations of the apparatus according to an aspect of the disclosure.

Furthermore, the present disclosure provides a computer program for classifying a brain tissue area as functional or non-functional during a stimulation of the brain. The computer program includes instructions which, when executed on a computer, cause the computer to receive information items about a performed stimulation, to receive images representing the brain tissue area, to check whether there is a change in perfusion in the brain tissue area on the basis of the received images, if the check yields that a change in perfusion is present to determine whether there is a correlation between the performed stimulation and the change in perfusion with the aid of the information items about the performed stimulation, and to classify the brain tissue area as functional if the presence of a correlation is determined and to classify the brain tissue area as non-functional if the presence of a correlation is not determined.

Endomicroscopic images of the brain tissue area with a spatial resolution of better than 20 µm, for example 10 µm, 5 µm, 3 µm, 1 µm, 0.7 µm or better, and a frame rate of at least 0.4 frames per second, in particular a frame rate of at least one frame per second, are received as images. The instructions included by the computer program prompt the computer to undertake the check as to whether a change in perfusion is present on the basis of the positions of certain tissue structures in at least one recorded image. Here, the positions of the specific tissue structures are the positions of two different tissue structures in the same image. The distance between these tissue structures is determined on the basis of the positions. A change in perfusion is then detected on the basis of a change in the distance.

The computer program according to an aspect of the disclosure allows a computer or any other data processing apparatus to be adapted to the execution of the computer-implemented method according to the disclosure.

Further configurations of the computer program include instructions which facilitate the adaptation of the computer or the other data processing apparatus to carrying out the functions which have been described in relation to the configurations of the apparatus according to an aspect of the disclosure and which are carried out by the configurations of the apparatus according to an aspect of the disclosure.

A non-volatile storage medium according to an aspect of the disclosure contains instructions stored thereon for classifying a brain tissue area as functional or non-functional during a stimulation of the brain. The stored instructions include such instructions which, when executed on a computer, prompt the computer to receive information items about a performed stimulation, to receive images representing the brain tissue area, to check whether there is a change in perfusion in the brain tissue area on the basis of the received images, if the check yields that a change in perfusion is present to determine whether there is a correlation between the performed stimulation and the change in perfusion with the aid of the information about the performed stimulation, and to classify the brain tissue area as functional if the presence of a correlation is determined and to classify the brain tissue area as non-functional if the presence of a correlation is not determined.

Endomicroscopic images of the brain tissue area with a spatial resolution of better than 20 μm, for example 10 μm, 5 μm, 3 μm, 1 μm, 0.7 μm or better, and a frame rate of at least 0.4 frames per second, in particular a frame rate of at least one frame per second, are received as images. Moreover, the stored information items include such instructions which, when executed on a computer, prompt the computer to undertake the check as to whether a change in perfusion is present on the basis of the positions of certain tissue structures in at least one recorded image. Here, the positions of the specific tissue structures are the positions of two different tissue structures in the same image. The distance between these tissue structures is determined on the basis of the positions. A change in perfusion is then detected on the basis of a change in the distance.

The non-volatile computer readable storage medium allows the computer program according to an aspect of the disclosure to be loaded onto a computer or any other data processing apparatus. Developments of the non-volatile computer readable storage medium can contain developments of the computer program according to an aspect of the disclosure.

According to a further aspect of the disclosure, a data processing device having a processor and at least one memory is moreover provided, wherein the processor is configured on the basis of instructions of a computer program stored in the memory to classify a brain tissue area as functional or as non-functional during a stimulation of the brain to receive information items about a performed stimulation, to receive images representing the brain tissue area, to check whether there is a change in perfusion in the brain tissue area on the basis of the received images, if the check yields that a change in perfusion is present to determine whether there is a correlation between the performed stimu-lation and the change in perfusion with the aid of the information about the performed stimulation, and to classify the brain tissue area as functional if the presence of a correlation is determined and to classify the brain tissue area as non-functional if the presence of a correlation is not determined.

The data processing apparatus according to an aspect of the disclosure receives endomicroscopic images of the brain tissue area with a spatial resolution of better than 20 μm, for example 10 μm, 5 μm, 3 μm, 1 μm, 0.7 μm, or better, and a frame rate of at least 0.4 frames per second, in particular a frame rate of at least one frame per second, as images. Moreover, the processor is configured on the basis of instructions of the computer program stored in the memory to undertake the check as to whether a change in perfusion is present on the basis of the positions of certain tissue structures in at least one recorded image. Here, the positions of the specific tissue structures are the positions of two different tissue structures in the same image. The distance between these tissue structures is determined on the basis of the positions. A change in perfusion is then detected on the basis of a change in the distance.

The data processing apparatus according to an aspect of the disclosure renders it possible to create an apparatus according to an aspect of the disclosure by combining the data processing apparatus with an endomicroscope and possibly with a stimulation apparatus. Here, the data processing apparatus according to an aspect of the disclosure can also be developed, in particular, in such a way that it facilitates the creation of the advantageous developments of the apparatus according to an aspect of the disclosure. In particular, the data processing apparatus according to an aspect of the disclosure can be a computer.

BRIEF DESCRIPTION OF THE DRAWINGS

The disclosure will now be described with reference to the drawings wherein.

DESCRIPTION OF EXEMPLARY EMBODIMENTS

Figure 1:
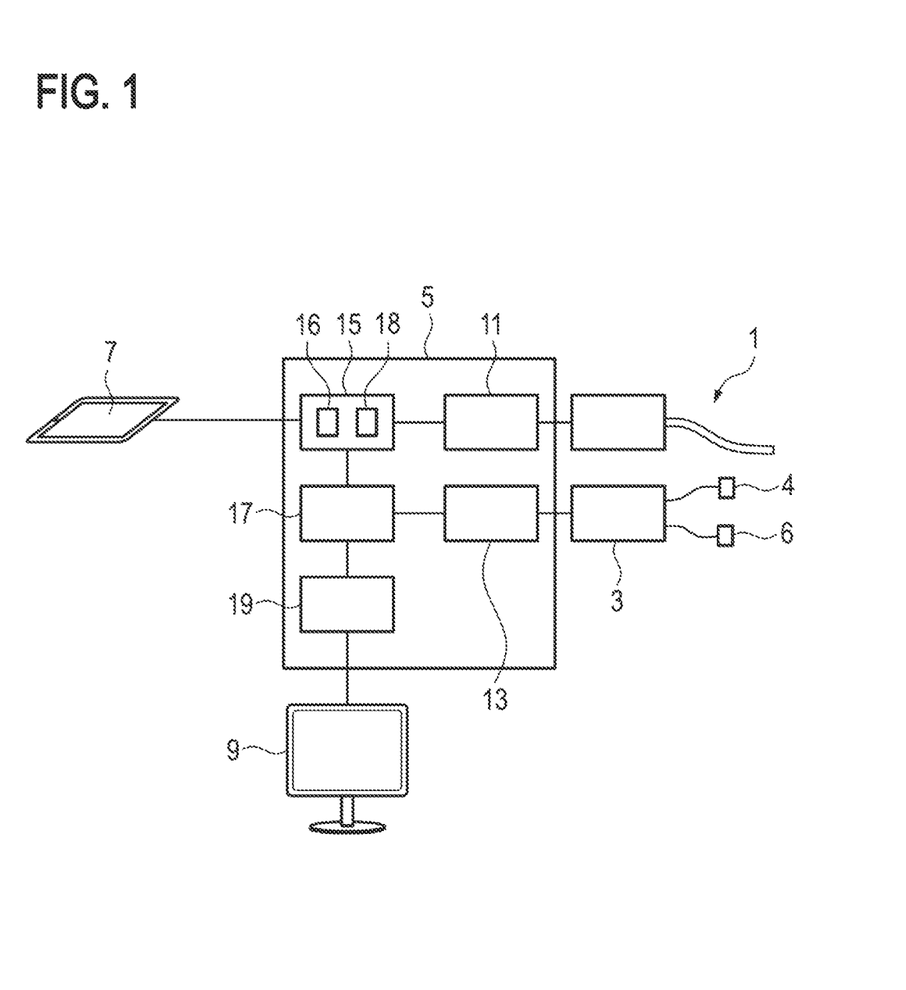
FIG. 1 shows a block diagram of an apparatus for classifying a brain tissue area as functional or non-functional according to an exemplary embodiment of the disclosure.

The present disclosure is described in detail below for explanatory purposes on the basis of exemplary embodiments. Here, FIG. 1 shows, in the form of a block diagram, an apparatus for classifying brain tissue areas as functional or non-functional. The apparatus includes an endomicroscope 1 as a recording device for recording images representing a brain tissue area, a nerve stimulator 3 for stimulating the peripheral nervous system of a patient as an electrical stimulation apparatus, and a data processing apparatus 5, with the aid of which the classification of a brain tissue area, which was imaged in a recorded image, as functional or non-functional is carried out. A dedicated data processing apparatus 5 is used in the present exemplary embodiment; it serves exclusively to detect changes in perfusion, to detect correlations between changes in perfusion and stimulations, and to classify brain tissue areas imaged in recorded images. The data processing apparatus 5 is connected to peripheral devices, specifically a tablet 7 as an input apparatus and a monitor 9 as an output apparatus. Moreover, further input and output apparatuses can be present, for example a keyboard, a voice input system, a loudspeaker, a headset, etc. Instead of the dedicated data processing apparatus 5, a computer can be used in other exemplary embodiments, which computer has been adapted with a computer program to the detection of changes in perfusion, to the detection of correlations between changes in perfusion and stimulations, and to the classification of brain tissue areas imaged in recorded images.

In the present exemplary embodiment, the data processing apparatus 5 includes an interface 11, with which the data processing apparatus 5 is connected to the endomicroscope 1 for receiving the images recorded with the latter. In this sense, the interface 11 forms a receiver unit for receiving the recorded images. A further interface 13 of the data processing apparatus 5 is connected to the nerve stimulator 3 in order to obtain from the nerve stimulator 3 information items about the stimulations performed. In this sense, the interface 13 forms a receiver unit for receiving information items about the stimulations performed. Furthermore, the data processing apparatus 5 includes a detection unit 15, with which changes in perfusion are detected in the represented brain tissue area on the basis of the images received by the endomicroscope 1, and a classification unit 17, which is connected to the detection unit 15 and the interface 13 via which the information items about the stimulation are received. The classification unit 17 checks whether there is a correlation between the performed stimulation and the detected change in perfusion. If the classification unit 17 determines a correlation, the brain tissue area represented in the received image is classified as functional. By contrast, if no correlation is determined, the brain tissue area is classified as non-functional.

In the present exemplary embodiment, an augmentation unit 19 is connected to the classification unit 17, said augmentation unit receiving from the classification unit 17 the image together with the associated classification result and marking each brain tissue area for which it has obtained a classification result, on the basis of which marking it is possible to recognize the classification result for the respective brain tissue area. By way of example, brain tissue areas classified as functional can be colored in a certain way in order to distinguish these from the brain tissue areas classified as non-functional. However, there is also the option of coloring both the brain tissue areas classified as functional and the brain tissue areas classified as non-functional, with the color of the brain tissue areas classified as functional differing from the color of the brain tissue areas classified as non-functional. Coloring both the brain tissue areas classified as functional and the brain tissue areas classified as non-functional facilitates a particularly high contrast representation of the differently classified brain tissue areas. The marked classified brain tissue areas are finally represented on the monitor 9. The latter displays an overview image which represents a plurality of brain tissue areas that are each marked in accordance with their classification. In this way, functional brain tissue areas can be emphasized in an overview image representing a tissue region.

The check as to whether a change in perfusion is present, undertaken by the detection unit 15, is implemented within the scope of the present disclosure on the basis of the positions of certain tissue structures in the recorded images. So that the tissue structures can be recognized in the recorded images, an endomicroscope 1 that is able to resolve structures of 0.7 µm is used in the exemplary embodiment. The resolution of the endomicroscope 1 can be lower in other exemplary embodiments. However, so that tissue structures can be recognized, a resolution of 20 µm or better, for example 10 µm or better, in particular 5 µm or better, typically 3 µm, specifically 1 µm or better is advantageous. An endomicroscope 1, as is used as an image recording device in the present exemplary embodiment, is described below with reference to FIGS. 2 and 3. In addition to the endomicroscope 1, FIG. 2 also shows a computer 37 which forms the data processing apparatus 5 in this exemplary embodiment. The computer 37 is a notebook containing a keyboard as an input device and a screen as an output device; however, it could also be realized by any other type of computer. In other computers, the monitor and the keyboard and further input and output devices may be present as peripheral devices.

Figure 2:
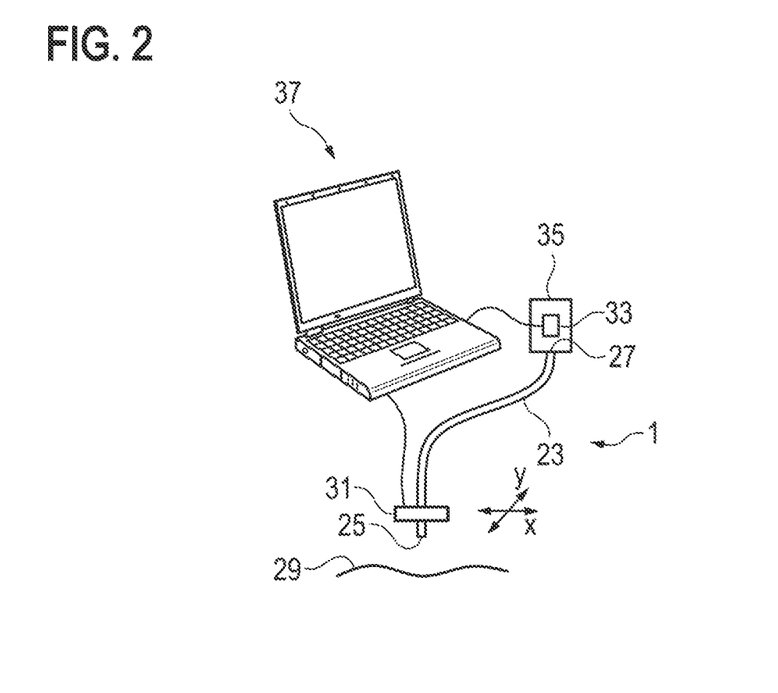
FIG. 2 shows an endomicroscope configured to carry out a scanning imaging method as an exemplary embodiment of a recording device for recording images representing a brain tissue area.

The endomicroscope 1 shown in FIG. 2 includes an optical fiber 23 with an input end 25 and an output end 27. The input end 25 faces the observation object 29 and it is located in a scanning device 31, with the aid of which the end 25 can be moved along two lateral directions, referred to as x-direction and y-direction below, with respect to the observation object 29. In particular, the scanning device can be realized with microelectromechanical systems (MEMS). By way of example, a scanning device using microelectromechanical systems is described in US 2016/0051131 A1. Reference is made to this document in respect of the structure of a suitable scanning device.

The second end of the optical fiber 23 faces a sensor 33, with which it is possible to capture luminous energy incident on the sensor 33. The sensor 33 is located in a housing 35, which is embodied as a separate module in the present exemplary embodiment, but which can also be embodied as a handle, and in which, moreover, a light source (not illustrated in the figure) for generating illumination light for illuminating the observation object 29 and an input coupling apparatus for coupling the illumination light into the second end 27 of the optical fiber 23 are housed. In particular, the light source can be a laser light source. However, the light source can also be arranged outside of the housing 35 and be connected to the latter by way of a light guide. Then, the output end of the light guide is situated in the housing 35. In this case, the input coupling apparatus couples the illumination light emerging from the output end of the light guide into the optical fiber 23. The illumination light can be white light, i.e., have a broadband spectrum, or light with a spectrum that consists of one or more narrowband spectral ranges, for example of one or more narrowband spectral ranges suitable for exciting a fluorescence in the observation object 29.

Illumination light coupled into the second end 27 of the optical fiber 23 is guided through the optical fiber 23 to the first end 25, from where the illumination light emerges in the direction of the observation object 29. Illumination light reflected by the observation object 29 or light excited by the illumination light and emitted by the observation object 29, for instance fluorescent light, enters into the first end 25 of the optical fiber 23 in turn and is guided from the latter to the second end 27, from where it emerges in the direction of the sensor 33. Moreover, focusing optical units can be located at, or in front of, the ends 25, 27 of the optical fiber 23 and these can be used to focus light onto the surface of the observation object 29 or onto the sensor 33. In particular, the endomicroscope 1 can be embodied as a confocal endomicroscope. In addition or as an alternative thereto, it can also be embodied as an endomicroscope for carrying out optical coherence tomography (OCT). Confocal microscopy and optical coherence tomography are well-known methods and are described in US 2010/0157308 A1 and U.S. Pat. No. 9,921,406 B2, for example. Therefore, the description of details in respect of confocal microscopy and in respect of optical coherence tomography is dispensed with in the scope of the present description. Instead, reference is made to US 2010/0157308 A1 and U.S. Pat. No. 9,921,406 B2.

Recording the image with the aid of the endomicroscope 1 is controlled with the aid of the computer 37 in the present exemplary embodiment. However, the control can also be implemented with a dedicated control device. The computer 37 used for controlling in the present exemplary embodiment is connected both to the scanning device 31 and to the sensor 33. In the present exemplary embodiment, the scanning device 31 is controlled by the computer 37 in such a way that the observation object 29 is scanned along a grid 39 with grid points 41 (cf. FIG. 3). In the present exemplary embodiment, the grid points 41 have a diameter of 0.7 µm; in other exemplary embodiments they can have other diameters, for example 20 µm, 10 µm, 5 µm, 3 µm, or 1 µm. At each scanned grid point 41 there is an illumination of the observation object 29 with illumination light and a recording of the reflected illumination light or of the light emitted by the observation object 29 on account of an excitation with the illumination light. Then, the computer produces an image from the reflected illumination light recorded at the grid points 41 or from the light emitted by the observation object recorded at the grid points 41, the pixel grid of said image corresponding to the grid 39 used during the scan and the maximum resolution of said image being given by the diameter of the grid points.

Figure 3:
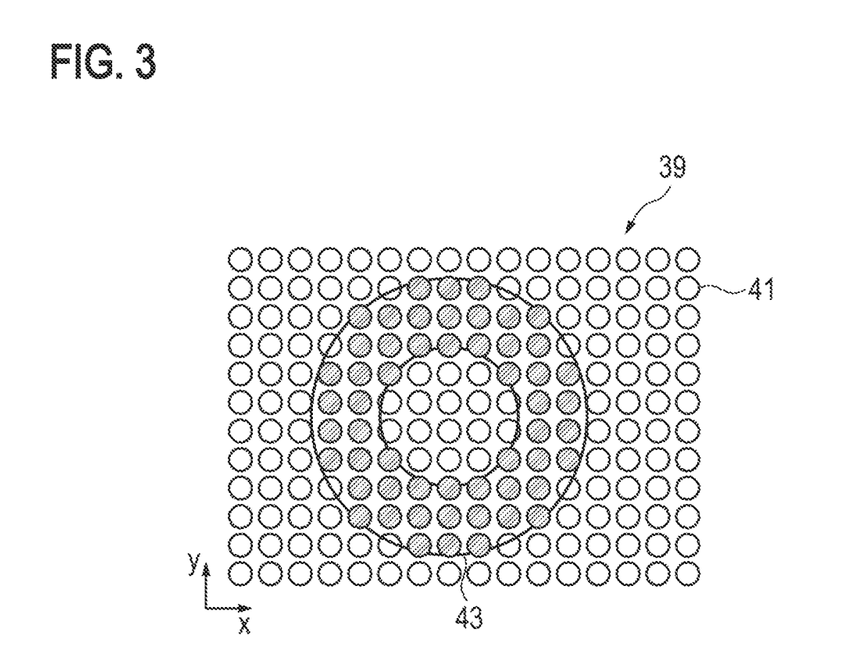
FIG. 3 shows a schematic illustration of an image recorded by an endomicroscope configured to carry out a scanning imaging method.

In the present exemplary embodiment, the grid includes grid lines which extend in the x-direction and grid columns which extend in the y-direction. Here, in the present exemplary embodiment, scanning of the observation object 29 is carried out line-by-line, i.e., in such a way that a line is scanned, i.e., there is a scan along the x-direction, and, after the line has been completed, there is an offset of the optical fiber 23 in the y-direction before a line extending in the x-direction is scanned again using the optical fiber 23, which has been offset in the y-direction. During the scanning procedure, the sensor 33 is exposed to each grid point 41, at which the optical fiber 23 is located at the time of a recording. In this way, an image of the observation object 29, as shown schematically in FIG. 3, is generated line-by-line with the aid of the sensor 33 and the scanning device 31. However, other scanning options are also possible, for example scanning along a helical scanning path.

FIG. 3 very schematically shows an image in which all grid points 41 of the grid 39 have been used when scanning the observation object 29. Here, FIG. 3 schematically shows a structure 43 of the observation object 29, which is represented by a ring for illustration purposes. Grid points 41 located over the structure 43 lead to a different signal on the sensor 33 than those grid points 41 that are not located over the structure 43. In FIG. 3, the signal generated by the grid points 41 located over the structure 43 is represented by hatched grid points 41. Using the small dimensions of the grid points 41 and correspondingly small distances between the grid points 41, as facilitated by the use of the optical fiber 23, it is possible to resolve tissue structures of the observation object 29. As a result, it is possible to recognize wall sections of capillary blood vessels in the recorded images. It is also possible to recognize erythrocytes, the dimensions of which are approximately 7.5 µm on average, in the recorded images.

On account of the large number of grid points 41 to be scanned linked with the high resolution, the production of a high-resolution image with the aid of the scanning imaging method requires a relatively long time, and so only relatively low frame rates can be obtained. In the present exemplary embodiment, frame rates of approximately one frame per second can be obtained at maximum resolution. To increase the frame rate there is the option of reducing the number of grid points 41 used during the scanning in order to increase the speed with which the scan can be carried out for an image. To this end, the computer 37 can act in controlling fashion on the scanning device 11 in such a way in the present exemplary embodiment that only certain lines are omitted when scanning along the grid 39. Expressed differently, only every n-th line is scanned during scanning. By way of example, if only every third line of the grid 39 is used during the scan, the frame rate can be increased approximately threefold. A further increase in the frame rate can be achieved if only every n-th grid point 41 is also scanned in each n-th line. By way of example, if only every third line is used during scanning and only every third grid point 41 is used in the utilized lines, the resolution of the image obtained is reduced by approximately a factor of 3. In the case of a maximum resolution of the endomicroscope of 0.7 µm, the reduced resolution would still be approximately 2.2 µm, which is sufficient to resolve tissue structures with a sufficient accuracy. In return, the frame rate would increase by approximately a factor of 9. Using an endomicroscope as per the present exemplary embodiment, it is possible to record brain tissue areas with dimensions of 500 µm×500 µm. Therefore, a section of a capillary blood vessel with a length of approximately 700 µm can be represented along the image diagonal. By way of example, this would allow flow speeds of erythrocytes of 0.7 mm/s to be captured in the case of a frame rate of 1 frame per second. If the frame rate is increased to approximately 9 frames per second on account of scanning only every third line and only using every third grid point in each scanned line, it is possible to capture flow speeds of erythrocytes of approximately 6 mm/s, which covers the typical speeds of erythrocytes in capillary vessels. Erythrocytes can be identified at a resolution of still approximately 2.2 µm.

Figure 4:
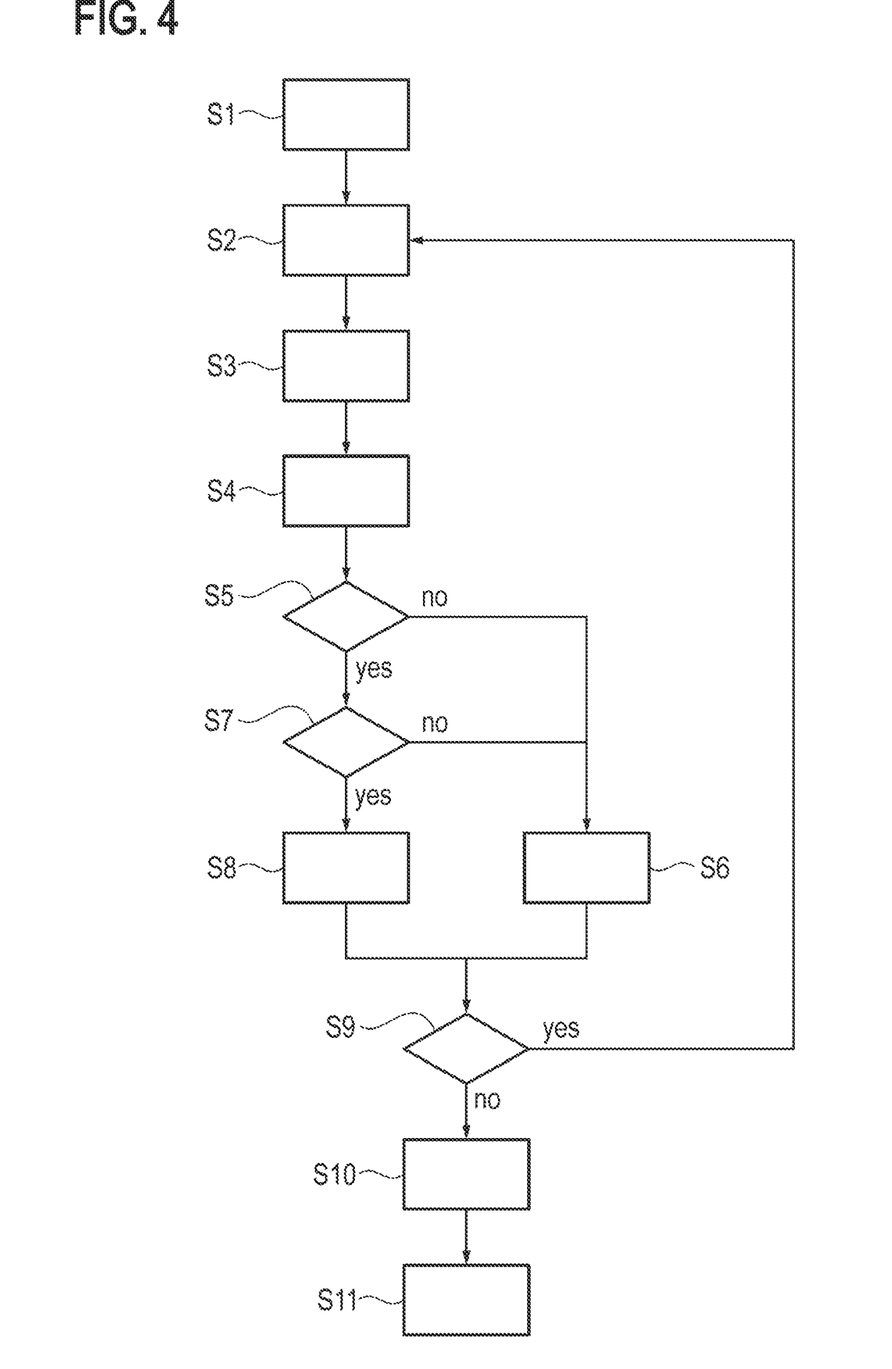
FIG. 4 shows a flowchart of a method for classifying a brain tissue area as functional or non-functional according to an exemplary embodiment of the disclosure.

An exemplary embodiment for the method according to the disclosure for classifying brain tissue areas as functional or non-functional is described below on the basis of the flowchart shown in FIG. 4.

After the method is started in step S1, a brain tissue area to be recorded is approached with the endomicroscope 1 in step S2. Then, image recording is started in step S3. During the image recording, the recorded images are each provided with a timestamp in the present exemplary embodiment. Moreover, the stimulation with the aid of the nerve stimulator 3 is started in step S3. In the present exemplary embodiment, the nerve stimulator 3 has a number of electrodes which are illustrated in exemplary fashion in FIG. 1 under the reference signs 4 and 6 and with the aid of which nerves of the peripheral nervous system are electrically stimulated, for example the median nerve, which is responsible for the motor control of the forearm muscles and some finger muscles and for the sensitive innervation of the palm of the hand and the thumb up to the inner side of the ring finger, or the trigeminal nerve, which is responsible for the sensitive perception in the face and for the motor system of face, oral cavity and masticatory muscles. Reference is made here to the fact that the median nerve and the trigeminal nerve are only specified in exemplary fashion for elucidating the procedure and that the stimulation is not restricted to the median nerve or the trigeminal nerve. Other nerves of the peripheral nervous system can also be stimulated depending on the brain region in which the brain tissue areas intended to be classified as functional or non-functional are situated. Moreover, the stimulation need not necessarily be implemented with a nerve stimulator 3. In the case of a conscious patient, the stimulation can also be implemented without a nerve stimulator by virtue of the patient being asked to carry out certain tasks, the performance of which leads to the stimulation of certain brain tissue areas. By way of example, a signal specifying the time of the start of a stimulation and a signal specifying the time of the end of a stimulation can be triggered manually, for instance, in this case.

Then, in step S4, the data processing system 5 receives the recorded images 45 from the endomicroscope 1 and information items about the performed stimulation from the nerve stimulator 3. These information items contain the respective start and end times of a stimulation in the present exemplary embodiment. In alternative embodiment variants, the information items might also contain the start time and the duration of a stimulation instead of the start time and the end time of a stimulation. It is likewise possible to couple the nerve stimulator 3 to the endomicroscope 1 in such a way that the nerve stimulator outputs a signal to the endomicroscope 1 at the start of a stimulation, following which the currently recorded image is labeled as the start image of the stimulation. Accordingly, a further signal can be output to the endomicroscope 1 at the end of the stimulation, said endomicroscope labeling the currently recorded image as the end image of the stimulation upon reception of this signal. In this case, the information items about the stimulation are contained in the images received from the endomicroscope 1. There is then no need to provide the images with a timestamp in this case.

Figure 5:
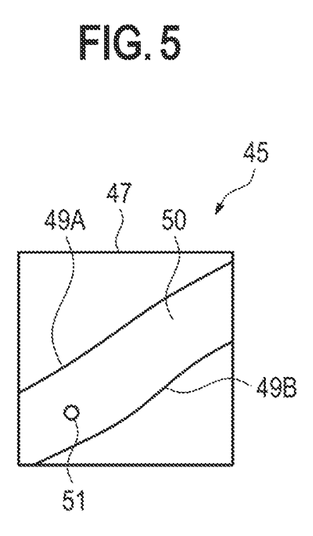
FIGS. 5 to 7 show a schematic illustrations of endomicroscopic images with tissue structures to be recognized therein.
Figure 6:
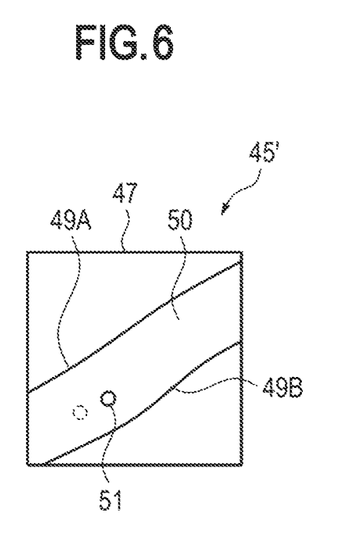
Figure 7:
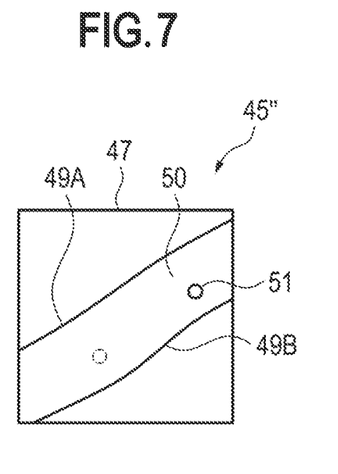

On the basis of the images 45 received in step S4, the detection unit 15 of the data processing system 5 then checks whether there is a change in the perfusion in the brain tissue area 47, of which the images have been recorded. To this end, the detection unit 15 in the present exemplary embodiment includes a recognition module 16, which is designed to recognize on the basis of morphological criteria tissue structures 49A, 49B, and 51 in the image 45 of the brain tissue area 47. To this end, use can be made of a trained neural network, for example, the latter having been trained using training data records which respectively contain images recorded by the endomicroscope 1 and information items about the image positions at which tissue structures 49A, 49B, and 51 can be recognized. However, it is also possible to detect certain tissue structures 49A, 49B, and 51 using conventional algorithms, for example by virtue of searching for intensity and/or color profiles that are characteristic for these tissue structures in the images. In the present exemplary embodiment, the recognition module 16 is embodied to recognize vessel walls 49A, 49B of capillary blood vessels 50 (cf. FIGS. 5 to 7). To detect a change in perfusion, the detection unit 15 checks whether there is a change in the distance between opposing vessel wall sections 49A, 49B in at least one capillary blood vessel 50 in the sequence of images 45, 45', and 45" recorded by the endomicroscope 1. A change in the distance between opposing vessel wall sections 49A, 49B of a capillary blood vessel 50 (cf. images 45' and 45" in FIGS. 6 and 7) is a signal for a change in perfusion. Here, attention is drawn to the fact that the opposing vessel wall sections 49A, 49B of a capillary blood vessel 50 can be recognized as two separate tissue structures in a two-dimensional image since only the section through the vessel walls is represented. Within this meaning, a change in perfusion is detected in the present exemplary embodiment on the basis of the position of the tissue structures representing the vessel wall sections 49A, 49B in the images 45, 45', 45".

In addition or as an alternative thereto, there is the option of determining a change in perfusion on the basis of the movement speed of erythrocytes 51, i.e., of red blood cells. In capillary blood vessels 50, erythrocytes 51 have movement speeds of 0.2 mm/s to 5 mm/s. In the case of, e.g., a resolution of 0.7 µm and a frame rate of 9 frames per second, it is possible to track erythrocytes in successive images even in the case of a movement speed of 5 mm/s in an image showing a brain tissue area 47 of 500 µm×500 µm. If a capillary blood vessel 50 in which the erythrocytes 51 move extends for example in a diagonal direction in the illustrated image field of 500 µm×500 µm, a capillary blood vessel length of 700 µm can be recognized in the images 45, 45', and 45". In the case of a frame rate of 9 frames per second and a movement speed of 5 mm/s, the time interval between two images is ⅑ second. In this ⅑ second, an erythrocyte traveling at 5 mm/s passes over a distance of 555 µm. Thus, the location of such a fast-moving erythrocyte 51 shifted by 555 mm/s from one image to the next (cf. FIGS. 6 and 7). In the case of a slower movement of the erythrocytes, the displacement from one image to the next is accordingly smaller (cf. FIGS. 5 and 6). Therefore, the detection unit 15 can determine the movement speed of the erythrocytes 51 on the basis of the displacement of an erythrocyte 51 in two successive images 45, 45', and 45". If there is a change in this movement speed, this indicates a change in perfusion. However, the change in perfusion can also be determined without calculating the movement speed since it is already the change in the distance between the positions of a certain erythrocyte 51 in successive images that signals a change in perfusion. In this sense, the positions of an erythrocyte 51 in two successive images represent positions of a tissue structure, specifically an erythrocyte 51, on the basis of which a change in perfusion can be detected. It is particularly advantageous if a change in perfusion is determined both on the basis of the change in the distance between the wall sections 49A, 49B of a capillary blood vessel 50 and on the basis of the change in the distance between the positions of an erythrocyte 51 in two successive images 45, 45', and 45", since the reliability of the detection of a change in perfusion can be increased by the presence of two independent information items.

Since global translations and/or rotations of the brain tissue area 47 may occur in the recorded images 45, 45', and 45" on account of physiological processes or on account of trembling when holding the endomicroscope 1, a registration of the images 45, 45', 45" can be implemented within the scope of step S5. To this end, the detection unit 15 includes a registration module 18 in the present exemplary embodiment, said registration module using one of the recorded images 45, 45', and 45" as a master image and fitting the other images 45, 45', and 45" to the master image with the aid of a rigid transformation in such a way that the rotational alignment and the relative translational position of the represented brain tissue area are the same in all images 45, 45', and 45".

If no change in perfusion is determined in step S5 on the basis of the recorded images 45, 45', and 45", the method advances to step S6, in which it classifies the brain tissue area 47 as non-functional. By contrast, if a change in perfusion is detected in step S5 on the basis of the recorded images, the method advances to step S7. Then, a check is carried out in step S7 with the aid of the classification unit 17 as to whether a correlation is present between the change in perfusion detected in step S5 and the information items about the stimulation. By way of example, if the images are provided with timestamps and the information about the stimulation contains the start time and end time of the stimulation or the start time and the stimulation duration, the classification unit 17 can check whether a time correlation is present between the start and/or the end of the stimulation and the occurrence of the change in perfusion. By way of example, such a correlation would be present if a change in perfusion occurs within a certain time period after the stimulation or after the end of the stimulation. In this case, the length of this time period depends on how quickly the stimulation leads to a change in perfusion. As a rule, this relationship is known from clinical studies. On the other hand, if the information about the stimulation is contained in the images themselves by virtue of the images recorded at the start of the stimulation and at the end of the stimulation having been marked accordingly, a functional brain tissue area 47 would be recognizable by virtue of a change in perfusion being recognizable in the marked image itself or in at least one certain image following the marked image. The image or the images in which the change in perfusion can be recognized in this case depends on the frame rate and the time that elapses between a stimulation and the change in perfusion induced by the stimulation.

If it is determined in step S7 that no correlation is present between the change in perfusion detected in step S5 and the information about the stimulation, the method advances to step S6, in which the brain tissue area 47 imaged in the images 45, 45', 45" is classified as non-functional. By contrast, if a correlation is determined in step S7, the brain tissue area 47 represented in the images 45, 45', and 45" is classified as functional in step S8.

Once the brain tissue area 47 imaged with the aid of the endomicroscope 1 has been classified as functional or non-functional, there is a query in step S9 as to whether further brain tissue areas should be classified. If so, the method returns to step S2, in which a further brain tissue area to be recorded is approached by the endomicroscope 1. Then, steps S3 to S8 are carried out again. In this case, the further brain tissue area can be approached by hand or in automated fashion on the basis of a path being prescribed, along which the input end 25 of the endomicroscope is displaced in order to be able to successively record different brain tissue areas.

Figure 8:
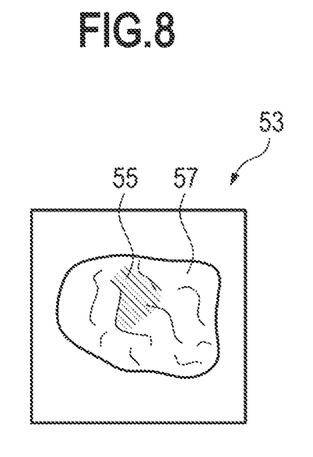
FIG. 8 shows an overview image that has been created on the basis of classified brain tissue areas.

If it is determined in step S9 that no further brain tissue area should be classified, the method advances to step S10, in which the classified brain tissue areas are combined in mosaic-like fashion to form an overview image 53, in which the functional brain tissue areas 55 differ from the non-functional brain tissue areas 57 (FIG. 8). By way of example, use can be made of a color code in which the functional brain tissue areas 55 are assigned a different color to the non-functional brain tissue areas 57. Here, it is also possible to only color the functional or the non-functional brain tissue areas. The respective other type of brain tissue areas can then be recognized on the basis of a lack of coloring. Moreover, instead of creating an overview image in mosaic-like fashion from the recorded brain tissue areas, there is the option of only using the classification of the recorded brain tissue areas to create a superposition image, which is superposed on an overview image obtained with a surgical microscope, for example, in order to label the functional brain tissue areas 55 in relation to the non-functional brain tissue areas 57 in any way.

Finally, the overview image 53 with the brain tissue areas marked in accordance with the classification thereof is represented on the monitor 9 or any other suitable indication apparatus. If a superposition image is produced in step S10, there also is the option, for example, of superposing the latter into the optical beam path of a surgical microscope such that a physician when viewing through the eyepieces of the surgical microscope sees an image of a brain tissue region in which the functional brain tissue areas can be distinguished from the non-functional brain tissue areas. After the representation of the overview image, in which the functional brain tissue areas are labeled in relation to the non-functional brain tissue areas, or vice versa, the method ends (step S11).

The disclosure can also be realized in the form of a computer program for classifying a brain tissue area as functional or non-functional during a stimulation of the brain, a non-volatile computer readable storage medium with instructions stored thereon for classifying a brain tissue area as functional or non-functional during a stimulation of the brain, or a data processing apparatus for classifying a brain tissue area as functional or non-functional during a stimulation of the brain.

The present disclosure has been described in detail on the basis of exemplary embodiments for explanatory purposes. However, a person skilled in the art recognizes that there can be deviations from the exemplary embodiments within the scope of the disclosure. Thus, for the classification of a brain tissue area, there is the option of, for example, carrying out a number of stimulations instead of a single stimulation, checking whether a change in perfusion is present for each of these stimulations, and, if so, checking whether a correlation is present between the change in perfusion and the received information about the respective stimulation. By averaging the results obtained on the basis of the stimulations, it is possible to reduce the statistical measurement inaccuracy and consequently improve the classification result. If a plurality of capillary blood vessels can be recognized in the recorded image of the brain tissue area, there is additionally or alternatively the option of determining whether a change in perfusion occurs for each of the capillary blood vessels to be identified and, if so, checking whether the change in perfusion correlates with the stimulation. Moreover, instead of merely classifying the imaged brain tissue area as functional or non-functional, there also fundamentally is the option of specifying a plurality of classes of functional brain tissue areas, which differ from one another, e.g., in terms of the strength of the change in perfusion following a stimulation or in the manner of how they correlate with the stimulation. By way of example, in the case of a time correlation, functional brain tissue areas which correlate at different time intervals with the stimulation, or which react with differently pronounced changes in perfusion to the stimulation could be distinguished from one another. To this end, use can be made of a neural network, for example, which has been trained using suitable training data records to recognize different changes in perfusion and/or recognize different correlations between changes in perfusion and a stimulation. By way of example, training data records which assign its characteristic change in perfusion and/or its characteristic correlation to the respective class can be used here for each class of functional brain tissue areas. Furthermore, there also is the option of using an algorithm or a trained neural network to check whether at least one capillary blood vessel can even be recognized in an imaged brain tissue area following the approach of the brain tissue area with the endomicroscope. Then, if a capillary blood vessel was not recognized, there would be the option of approaching other brain tissue areas until a brain tissue area is found in which at least one capillary blood vessel can be recognized in the recorded endomicroscopic image. Since, as described, numerous modifications of the exemplary embodiments are possible, the present disclosure should not be restricted by the exemplary embodiments but only by the attached claims.

LIST OF REFERENCE NUMERALS

1 Endomicroscope
3 Neurostimulator
4 Electrode
5 Data processing system
6 Electrode
7 Tablet
9 Monitor
11 Interface
13 Interface
15 Detection unit
16 Detection module
17 Classification unit
18 Registration module
19 Augmentation apparatus
23 Optical fiber
25 First end
27 Second end
29 Observation object
31 Scanner
33 Sensor
35 Housing
37 Computer
41 Grid point
43 Structure
45 Endomicroscopic image
47 Brain tissue area
49 Vessel wall
50 Capillary blood vessel
51 Erythrocyte
53 Overview image
55 Functional brain tissue areas
57 Non-functional brain tissue areas
S1 Start
S2 Approach of brain tissue area
S3 Stimulation and image recording
S4 Reception of images and information items about the stimulation
S5 Check whether a change in perfusion is present
S6 Classification as non-functional
S7 Check whether a correlation between a detected change in perfusion and the stimulation is present
S8 Classification as functional
S9 Check whether further brain tissue areas should be classified
S10 Create an augmented overview image
S11 End

What is claimed is:

1. An apparatus for classifying a brain tissue area as functional or non-functional by a stimulation of a brain, the apparatus comprising:
a receiver unit configured to receive information about a performed stimulation,
a recording device configured to record images which represent the brain tissue area,
a detection unit configured to detect a change in perfusion in the brain tissue area based on recorded images, and
a classification unit configured to:
determine from the information about the performed stimulation whether there is a correlation between the performed stimulation and the detected change in perfusion,
classify the brain tissue area as functional when it determines a correlation, and
classify the brain tissue area as non-functional when it does not determine a correlation,
wherein the recording device is an endomicroscope for recording endomicroscopic images of the brain tissue area with a spatial resolution better than 20 μm and a frame rate of at least 0.4 frames per second, and
wherein the detection unit is further configured to:
detect a change in perfusion based on positions of certain tissue structures in the recorded images, wherein the positions of the certain tissue structures are the positions of two different tissue structures in a same image,
determine a distance between the two different tissue structures based on the positions, and
detect a change in perfusion based on a change in the distance.

2. The apparatus as claimed in claim 1, wherein:
the positions of the certain tissue structures comprise the positions of the same tissue structure in at least two images recorded at time intervals, and
the detection unit is further configured to determine the change in a position of the tissue structure in the at least two images recorded at time intervals and to determine a change in perfusion based on the determined change in the position.

3. The apparatus as claimed in claim 2, wherein the detection unit is further configured to:
determine a movement speed of the tissue structure from the determined change in the position of the tissue structure in the at least two images recorded at time intervals, and
detect a change in profusion based on a change in the determined movement speed.

4. The apparatus as claimed in claim 1, wherein the detection unit comprises an input apparatus which permits tissue structures of the brain tissue area represented in the image to be marked in a recorded image.

5. The apparatus as claimed in claim 1, wherein the detection unit comprises a recognition module configured to recognize at least one type of tissue structures of the brain tissue area represented in a recorded image.

6. The apparatus as claimed in claim 1, wherein the detection unit comprises a registration module configured to register the recorded images to one another.

7. The apparatus as claimed in claim 1, further comprising an electrical stimulation apparatus for electrical stimulation of the brain.

8. The apparatus as claimed in claim 1, further comprising an augmentation apparatus configured to label brain tissue areas classified as functional in an overview image which represents a tissue region with a number of brain tissue areas.

9. A method for classifying a brain tissue area as functional or non-functional during a stimulation of a brain, the method comprising:
receiving information about a performed stimulation,
recording images which represent the brain tissue area,
determining whether there is a change in perfusion in the brain tissue area based on recorded images,
when it is determined that the change in perfusion is present, determining whether there is a correlation between the performed stimulation and the change in perfusion from information about the performed stimulation; and
classifying the brain tissue area as functional when a presence of a correlation is determined and classifying the brain tissue area as non-functional when the presence of a correlation is not determined,
wherein endomicroscopic images of the brain tissue area with a spatial resolution better than 20 µm and a frame rate of at least 0.4 frames per second are recorded as the images and determining whether the change in perfusion is present is undertaken based on the positions of certain tissue structures in at least one recorded image,
wherein the positions of the certain tissue structures are the positions of two different tissue structures in the same image,
wherein the distance between the two different tissue structures is determined based on the positions, and
wherein a change in perfusion is detected based on a change in the distance.

10. The method as claimed in claim 9, further comprising:
classifying a plurality of brain tissue areas and marking the classified brain tissue areas in an overview image based on their classification.

11. A computer-implemented method for classifying a brain tissue area as functional or non-functional during a stimulation of a brain, the computer-implemented method comprising:
receiving information items about a performed stimulation,
receiving images which represent the brain tissue area,
determining whether there is a change in perfusion in the brain tissue area based on the images received,
when it is determined that the change in perfusion is present, determining whether there is a correlation between the performed stimulation and the change in perfusion from information about the performed stimulation, and
classifying the brain tissue area as functional when a presence of a correlation is determined and otherwise classifying the brain tissue area as non-functional when the presence of a correlation is not determined,
wherein endomicroscopic images of the brain tissue area with a spatial resolution better than 20 µm and a frame rate of at least 0.4 frames per second are received as the images and determining whether the change in perfusion is present is undertaken based on the positions of certain tissue structures in at least one recorded image,
wherein the positions of the certain tissue structures are the positions of two different tissue structures in the same image,
wherein the distance between the two different tissue structures is determined based on the positions, and
wherein a change in perfusion is detected based on a change in the distance.

\* \* \* \* \*

UNITED STATES PATENT AND TRADEMARK OFFICE
CERTIFICATE OF CORRECTION

PATENT NO. : 11,836,920 B2
APPLICATION NO. : 17/206059
DATED : December 5, 2023
INVENTOR(S) : Christoph Hauger, Stefan Saur and Gerald Panitz It is certified that error appears in the above-identified patent and that said Letters Patent is hereby corrected as shown below:

In the Specification

For BACKGROUND, Column 1:
Line 57: Replace "Oelschlagel" with "Oelschlägel"

Signed and Sealed this
Second Day of September, 2025

Coke Morgan Stewart
*Acting Director of the United States Patent and Trademark Office*